US006846314B2

United States Patent
Shapira

(10) Patent No.: US 6,846,314 B2
(45) Date of Patent: Jan. 25, 2005

(54) METHOD AND APPARATUS FOR EXTRACTING BONE MARROW

(76) Inventor: Ira L. Shapira, 3223 Dato, Highland Park, IL (US) 60035

( * ) Notice: Subject to any disclaimer, the term of this patent is extended or adjusted under 35 U.S.C. 154(b) by 435 days.

(21) Appl. No.: 10/020,635

(22) Filed: Dec. 14, 2001

(65) Prior Publication Data

US 2003/0078586 A1 Apr. 24, 2003

Related U.S. Application Data

(60) Continuation-in-part of application No. 09/631,018, filed on Aug. 2, 2000, now Pat. No. 6,358,252, which is a continuation of application No. 09/271,481, filed on Mar. 17, 1999, now Pat. No. 6,110,176, which is a division of application No. 08/886,173, filed on Jul. 1, 1997, now Pat. No. 5,913,859.

(51) Int. Cl.[7] ............................ A61B 17/16; A61M 1/00
(52) U.S. Cl. .......................................... 606/80; 604/35
(58) Field of Search ................... 433/96, 91, 102–104, 433/122, 124, 125; 606/170, 79–81, 180, 159; 604/35, 22; 600/565, 566, 564, 568

(56) References Cited

U.S. PATENT DOCUMENTS

| | | | |
|---|---|---|---|
| 2,426,535 A | 8/1947 | Turkel | 128/2 |
| 2,496,111 A | 1/1950 | Turkel | 128/2 |
| 3,587,560 A | 6/1971 | Glassman | 128/2 |
| 3,745,655 A | 7/1973 | Malmin | 32/40 R |
| 3,807,048 A | 4/1974 | Malmin | 32/40 R |
| 3,816,921 A | 6/1974 | Malmin | 32/40 R |
| 3,863,635 A | 2/1975 | Swatman | 128/276 |
| 3,871,099 A | 3/1975 | Kahn | 32/40 R |
| 3,937,222 A | 2/1976 | Banko | 128/305 |
| 4,176,453 A | 12/1979 | Abbott | 433/82 |
| 4,266,555 A | 5/1981 | Jamshidi | 128/753 |
| 4,469,109 A | 9/1984 | Mehl | 128/753 |
| 4,487,209 A | 12/1984 | Mehl | 128/754 |
| 4,541,423 A * | 9/1985 | Barber | 606/80 |
| 4,543,966 A | 10/1985 | Islam et al. | 128/754 |
| 4,564,374 A | 1/1986 | Hofmann | 55/57 |
| 4,840,184 A | 6/1989 | Garg | 128/753 |
| 4,922,602 A | 5/1990 | Mehl | 29/460 |
| 5,012,818 A | 5/1991 | Joishy | 128/754 |
| 5,122,153 A | 6/1992 | Harrel | 606/180 |
| 5,269,785 A * | 12/1993 | Bonutti | 606/80 |
| 5,295,830 A | 3/1994 | Shen et al. | 433/116 |
| 5,357,974 A | 10/1994 | Baldridge | 128/754 |
| 5,403,276 A | 4/1995 | Schechter et al. | 604/22 |
| 5,531,596 A | 7/1996 | Melde | 433/104 |
| 5,601,560 A * | 2/1997 | Del Rio et al. | 606/80 |
| 5,667,490 A * | 9/1997 | Keith et al. | 604/22 |
| 5,913,859 A | 6/1999 | Shapira | 606/80 |
| 6,110,176 A | 8/2000 | Shapira | 606/80 |

FOREIGN PATENT DOCUMENTS

| | | |
|---|---|---|
| WO | WO 03/013336 | 2/2003 |
| WO | WO 03/039311 A1 | 5/2003 |

OTHER PUBLICATIONS

Shapira, U.S. application Ser. No. 09/631,018, filed Aug. 2, 2000.

* cited by examiner

Primary Examiner—Kevin T. Truong
Assistant Examiner—D. Jacob Davis
(74) Attorney, Agent, or Firm—Marshall, Gerstein & Borun LLP

(57) ABSTRACT

Methods and apparatus are presented for extracting and collecting bone material from an extraction site of a patient. The method and apparatus further provides a readily accessible, and easily harvested, source of bone material without the drawbacks of current extraction methods.

8 Claims, 6 Drawing Sheets

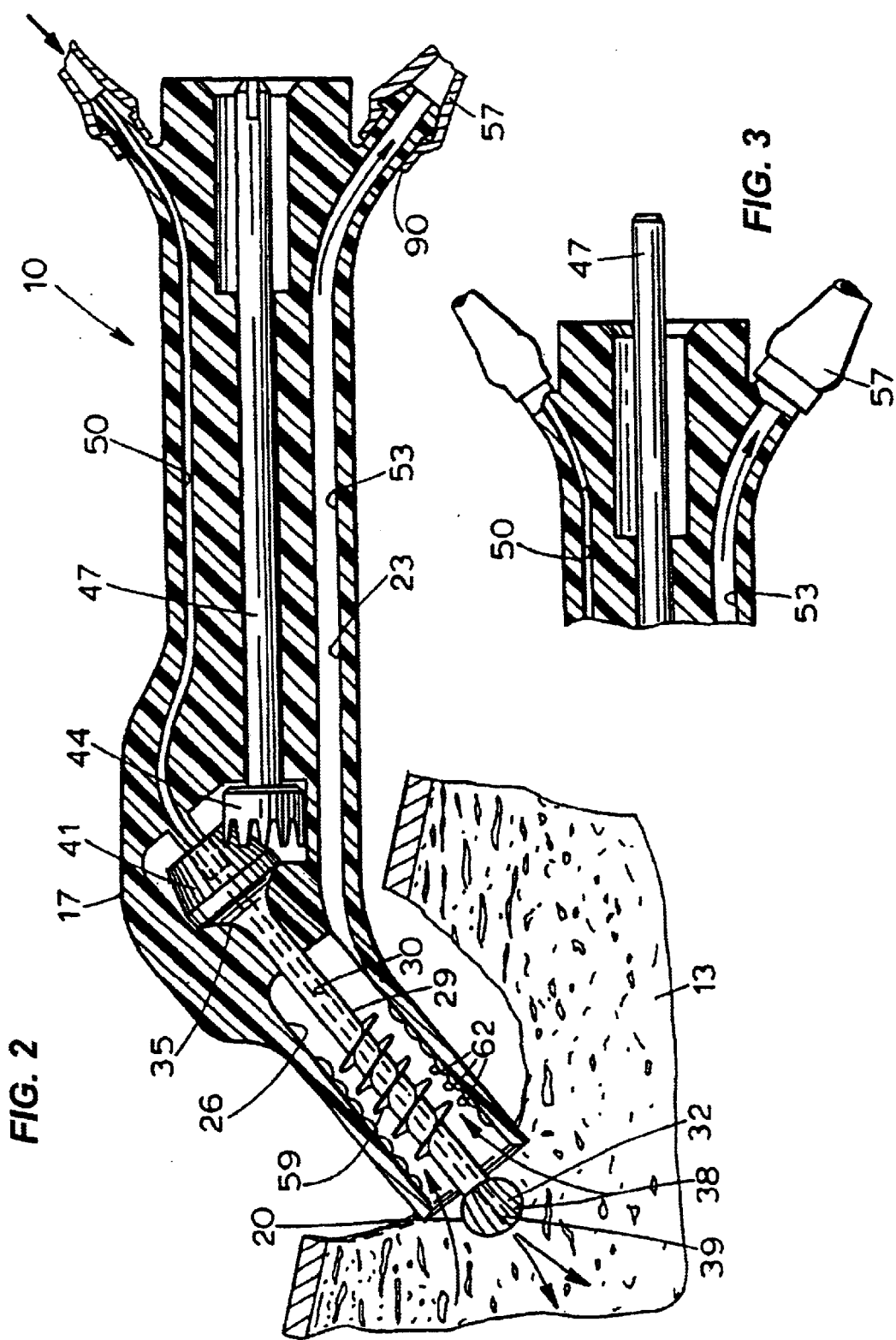

METHOD AND APPARATUS FOR EXTRACTING BONE MARROW

CROSS-REFERENCE TO RELATED APPLICATIONS

This is a continuation-in-part of U.S. application Ser. No. 09/631,018, filed Aug. 2, 2000, now U.S. Pat. No. 6,358,252 which is a continuation of U.S. application Ser. No. 09/271,481, filed Mar. 17, 1999, now U.S. Pat. No. 6,110,176, which is a division of U.S. application Ser. No. 08/886,173, filed Jul. 1, 1997, now U.S. Pat. No. 5,913,859.

FIELD OF INVENTION

The present invention relates generally to methods and apparatus for recovering bone material, such as bone marrow, bone, and contiguous tissue, from a patient and subsequent collection and storage.

BACKGROUND OF THE INVENTION

There are a number of diseases in which the bone marrow is defective, such as aplastic anemia, some forms of leukemia, and deficiencies in the bone marrow caused by cancer treatments with drugs and irradiation. The treatment of choice for these diseases is bone marrow transplantation, provided a genetically compatible donor can be found. For instance, bone marrow transplants are significantly reducing the death toll from childhood leukemias.

Bone marrow, also called myeloid tissue, is a soft, gelatinous tissue that fills the cavity of the bones. Human bone consists of a hard outer cortex and a soft medullary cavity that contains bone marrow. Bone marrow consists of stroma, or supporting tissues which have spaces packed by blood cells. Bone marrow is either red or yellow, depending upon the preponderance of vascular (red) or fatty (yellow) tissue. In humans, the red bone marrow forms all of the blood cells with the exception of the lymphocytes, which are produced in the marrow and reach their mature form in the lymphoid organs. Yellow bone marrow serves primarily as a storehouse for fats, but may be converted to red marrow under certain conditions, such as severe blood loss or fever. At birth, and until about the age of seven, all human marrow is red, as the need for new blood formation is high. Thereafter, fat tissue gradually replaces the red marrow, which in adults is found in the vertebrae, hips, breast bone, ribs, and skull, and at the ends of the long bones of the arms and legs, other cancellous, or spongy bones, and the central cavities of the long bones. In mammals, blood formation in adults takes place predominantly in the marrow. Because the white blood cells produced in the bone marrow are involved in the body's immune defenses, marrow transplants have been used to treat certain types of immune deficiencies. The sensitivity of marrow to damage by radiation and some anticancer drugs accounts for the tendency of these treatments to impair immunity.

Bone marrow transplants can be divided into three groups according to the source of the marrow for transplantation. They are called autologous, syngeneic, or allogeneic. Autologous transplantation means that the bone marrow has been received directly from the recipient, and will be an exact genetic match. A syngeneic transplant comes from an identical twin of the recipient and will also be an exact genetic match. However, for allogeneic transplants, the bone marrow is provided by another person, and the possibility of exact genetic matching is very low.

It is reported that approximately 12,000 bone marrow transplants were performed in 1992, approximately half of which were allogeneic and half autologous. Autologous transplantation has grown significantly during the past several years as improvements in procedures are made. The number of patients receiving allogeneic transplants is also rising due in large part because donor registries have increased the number of readily available donors. Advances in bone marrow transplantation techniques will likely continue to expand the use of the bone marrow transplant procedure.

Generally, the recipient's sibling or parent will serve as the best source as the donor because of the high possibility of genetic matching. However, there are many cases where neither the parent nor the sibling will be a compatible genetic match for the recipient. There has been a recent increase in the use of bone marrow from unrelated donors which can provide genetic compatibility between the donor and recipient. This increase has been made possible through the existence of large bone marrow registries, such as the National Marrow Donor Program, and the American Bone Marrow Donor Registry. The drawback to these registries are the insufficient number of donors that genetically match closely enough with potential recipients to be of use.

The success of the bone marrow transplantation technique depends heavily on genetically cross-matching the donor marrow cells to those of the recipient to prevent rejection. There is a significant tendency for the recipient patient to reject an allografted marrow because parts of the donor marrow will attack their new host. There is an additional hazard because immune system cells in a marrow graft can react against the patient's tissues, causing serious and sometimes fatal graft versus host disease. The ability to accept a bone marrow transplant (graft) from a donor, is dependent on the recipient sharing all of the donor's histocompatibility genes. To avoid graft versus host rejection in the past, special immunosuppressive treatment has been given. The use of monoclonal antibodies to selectively remove harmful lymphocytes from the donor marrow has been successful in some cases to prevent graft versus host disease. However, the risk remains that unless the bone marrow source is from the patient himself, an identical twin, sibling, parent, or other genetically compatible donor, that the bone marrow transplantation cannot take place because it will result in graft versus host rejection, and the failure of the treatment, and possibly the death of the recipient.

Therefore, there is a significant need to collect and store genetically compatible bone marrow for use in cases where bone marrow transplantation is necessary to save the life of an individual. Because of the significant possibility that a donor cannot be found which is a close genetic match to the recipient, there is a need to collect and store an individual's own bone marrow while that individual is still healthy. If this is done, there will be a complete genetic match, and the dangers of graft versus host rejection will be eliminated which increases the success of the treatment.

The collection of bone marrow for transplantation purposes is usually accomplished by inserting a needle into a donor's hip or pelvic bone. Several small incisions are made in the pelvic area, and the needle is inserted through these incisions approximately 25 to 30 times to withdraw the bone marrow from the bones. The extraction process typically lasts at least one hour or more, or until approximately 500 to 1000 milliliters of the donor's marrow is withdrawn.

The donor will fully recover in approximately a few weeks when all the donated marrow has been replaced within the body. However, the extraction process is painful and there is typically soreness around the incisions until healing can occur. Typically, the donors also feel fatigued for some time after the procedure. The side effects to having donated bone marrow can vary from donor to donor. Infection from the incision is always a possibility. Additionally, blood loss can also occur, and proper medical attention is required. It is recommended that donors routinely store supplies of their own blood for infusion during and after the extraction procedure in cases of emergencies.

Bone marrow can be obtained through biopsy or aspiration from the sternum or the calvarium in adults, and in long bones, such as the femur and tibia, in adolescents. Biopsy needles for extraction of solid bone marrow are known. Examples of such biopsy needles are U.S. Pat. Nos. 2,991,692; 2,426,535; 2,496,111; 4,272,676; 4,266,555; 4,543,966; 4,487,209; 4,840,184; and 4,922,602, which show the overall structure and orientation of the components. Needles used for aspiration of liquid bone marrow are disclosed in U.S. Pat. No. 4,469,109. Needles designed to both biopsy and aspirate bone marrow are disclosed in U.S. Pat. Nos. 2,496,111; 3,587,560; 5,012,818; and 5,357,974.

There is a need for bone marrow extraction techniques that avoid the considerable inconvenience, discomfort, and pain due to current bone marrow extraction procedures and aspiration methods. Therefore, there is also a need to provide a method and apparatus to obtain both solid and liquid bone marrow from a donor with minimal intrusion and pain. There is also a need for the bone marrow to be stored for later use and is accomplished with relative ease.

BRIEF DESCRIPTION OF THE DRAWINGS

FIG. 2 is an enlarged, fragmentary sectional view of the embodiment of FIG. 1;

FIG. 3 is an enlarged, fragmentary sectional view of an alternative embodiment of the apparatus constructed in accordance with the teachings of the present invention;

DETAILED DESCRIPTION

Figure 1:
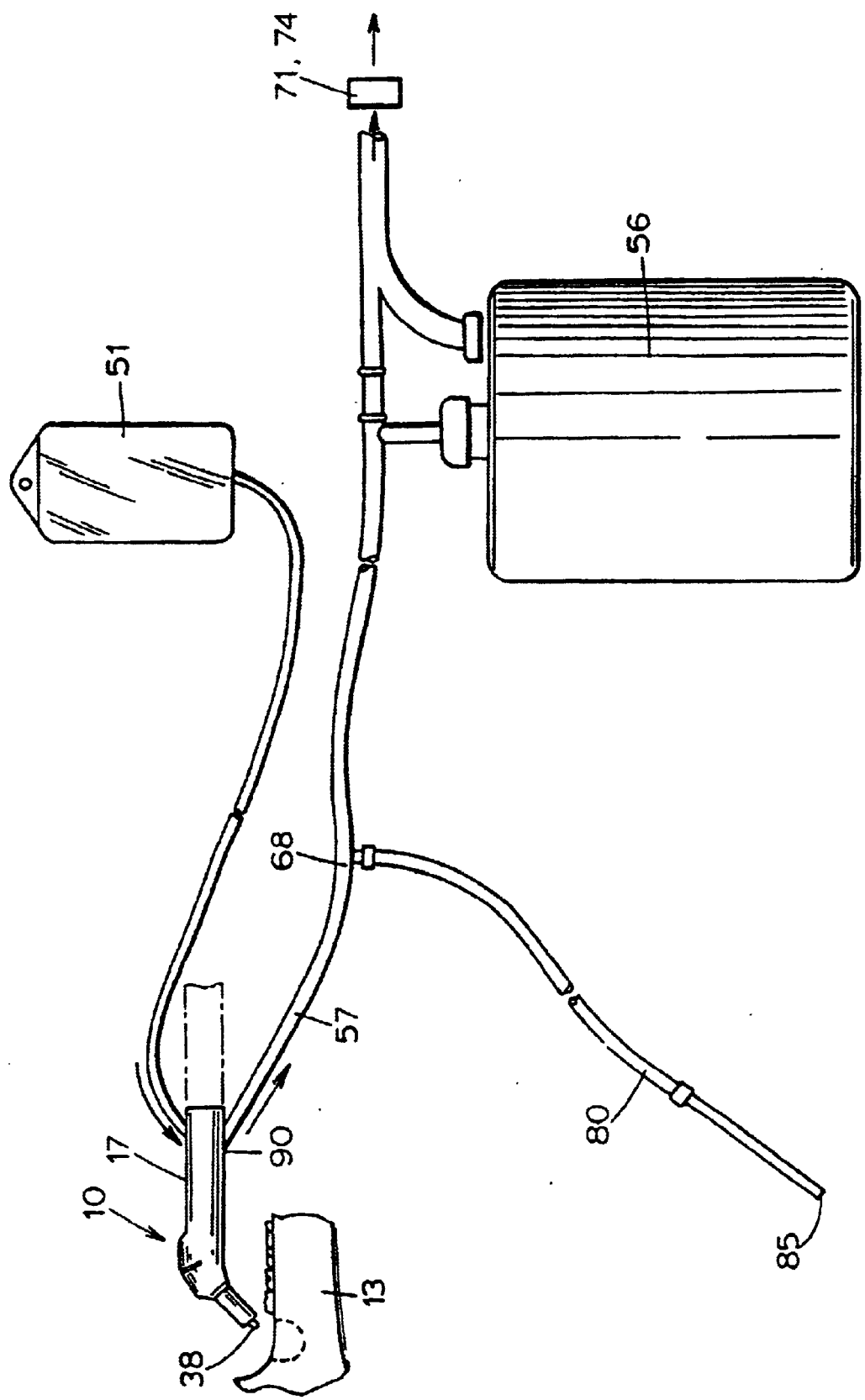
FIG. 1 is a side elevational view of one embodiment of a bone marrow extraction apparatus constructed in accordance with the teachings of the present invention.

FIG. 1 illustrates the principles and concepts of a bone marrow extraction apparatus well adapted for use according to the invention. Shown in FIGS. 1 and 2 is an apparatus 10 capable of boring a hole in a jawbone 13 and extracting bone marrow therefrom. The apparatus 10 comprises a housing 17, structure 20 attached to the housing 17 for extracting bone marrow from an extraction site, and structure 23 for collecting bone marrow extracted from the extraction site. While the embodiment of FIGS. 1 and 2 is illustrated and described herein for extracting marrow from a patient's jaw, it will be appreciated that the apparatus and methods may be used to extract marrow or other bone material, such as bone and contiguous tissue (including dental pulp) from other collection sites, as described in greater detail below.

The housing 17 has a cavity 26. A hollow shaft 29 having a conduit 30 and first and second end portions 32 and 35 is rotatably mounted in the housing 17 with the end portion 35 being disposed in the cavity 26. The end portion 32 includes a bur 38 having a cutting flute 39 for boring a hole in the jawbone 13. A beveled gear 41 is attached to the second end portion 35 of the hollow shaft 29. While, in the current embodiment, the hollow shaft 29 is provided integrally with the beveled gear 41, it will be appreciated that the hollow shaft 29 may be removably attached to the beveled gear 41 to facilitate bur replacement, as described more fully below with respect to the embodiment of FIG. 5. A drive gear 44 is matingly engaged to the beveled gear 41. The drive gear 44 is connected by a shaft 47 to an electrical motor, a pneumatic motor, or other suitable equipment (not shown) for driving the drive gear 44. The shaft 47 may be connected to the motor or other drive source by any feasible mechanical or other connection means. By engaging the shaft 47, the drive source rotates the shaft 47 so as to cause rotation of bur 38. As shown in FIG. 3, the shaft 47 may be adapted to be driven by a standard "E" motor.

The housing 17 may have a first passage 50 in communication with the hollow shaft 29. The first passage 50 is for passing irrigation fluid to the extraction site. The irrigation fluid passes through the passage 50 and then through the conduit 30 to the extraction site. The irrigation fluid cools the extraction site and adds liquid to the extracted fluids and solids to facilitate removal by suction. A source 51 (FIG. 1) of irrigation fluid may be connected to the housing 17 so that the source 51 is in communication with the first passage 50. The housing 17 has a second passage 53 in communication with the cavity 26. The second passage 53 is for passing bone marrow from the cavity 26 to a collection device 56 (FIG. 1). While the embodiment illustrated at FIG. 1 includes the first passage 50 for irrigation, it will be appreciated that the first passage 50 is not required and the apparatus may be used without irrigation, as described in greater detail below with respect to the embodiments of FIGS. 5 and 6.

A suction tube 57 may be connected to the second passage 53 for extracting solid bone marrow from the medullary cavity of the donor. The rotating bur 38 and the suction tube 57 are preferably detachably connectible to the housing. The housing 17 may be a hand-held power unit. However, while the housing 17 may be formed in a generally cylindrical handle-type configuration as shown in FIG. 1, such apparatus may be of other forms, including a pistol grip-type configuration (not shown).

Apparatus 10 may include structure for breaking up bone marrow into smaller particles prior to the entry of the particles into the second passage 53. For example, a spiral cutting blade 59 may be attached to the outer surface of the hollow shaft 29 for breaking up particles while the hollow shaft 29 rotates. Additionally or alternatively, the cavity 26 may be defined by walls having ridges 62. The ridges 62 break up the bone marrow into smaller particles as the particles pass through the cavity 26 into the second passage 53.

Figure 4:
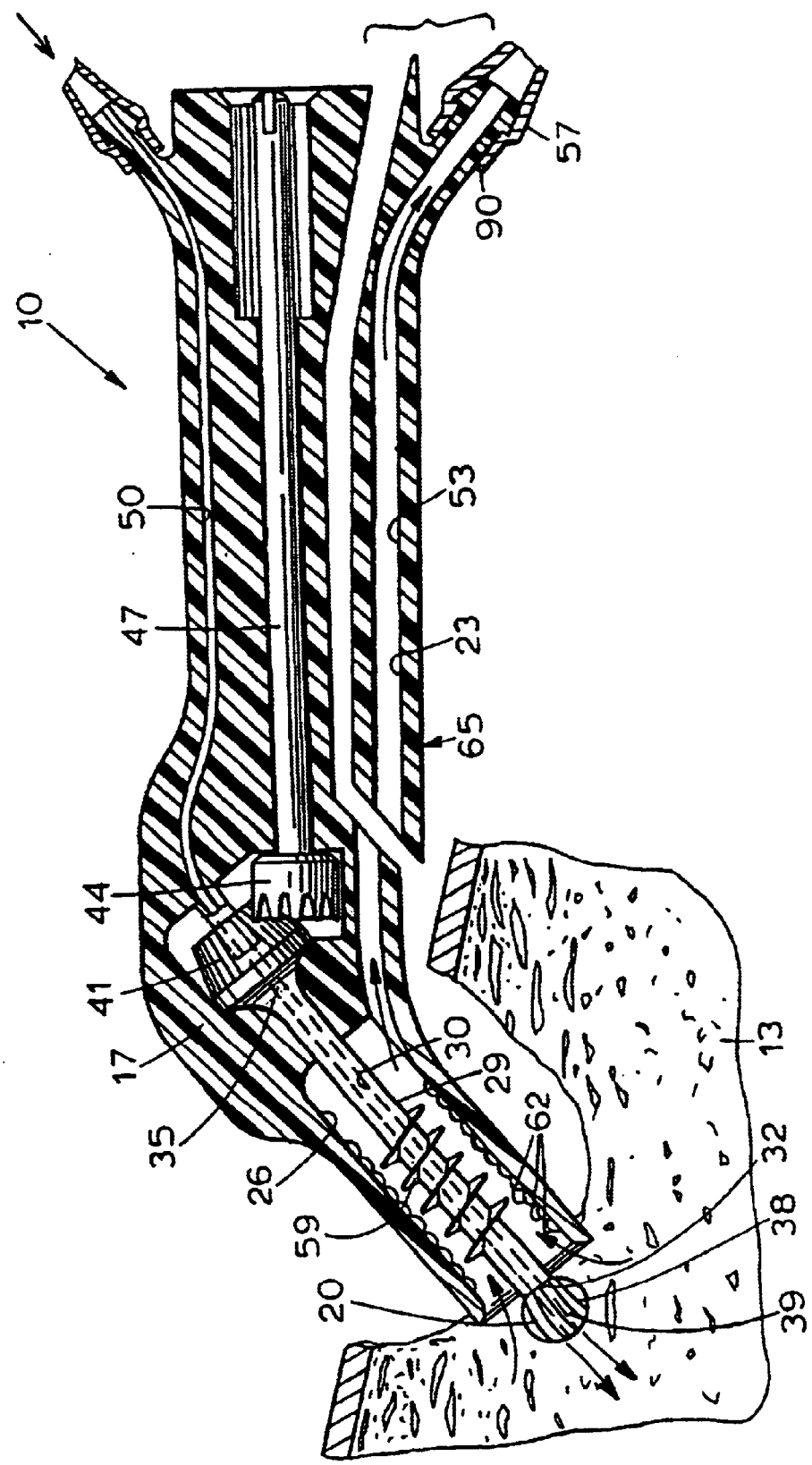
FIG. 4 is an enlarged, fragmentary sectional view of an alternative embodiment of the apparatus constructed in accordance with the teachings of the present invention.

As shown in FIG. 4, the housing 17 may have a detachable portion 65. At least a part of the second passage 53 is defined in the detachable portion 65. Alternatively, the second passage 53 may be connected to the outside portion of the housing 17 of FIGS. 2 and 4.

The suction tube 57, which includes an integral valve 68 (FIG. 1), is attached to a vacuum source 71 (shown schematically in FIG. 1) at one end and a suction tip (not shown) at the other end. The integral valve 68, which comprises a housing and a pivotal obturator, permits an operator of the apparatus to selectively produce suction through the suction tube 57 with one hand. See U.S. Pat. No. 5,295,830.

A vacuum source 74 (FIG. 1) withdraws solid and liquid bone marrow from the medullary cavity into the suction tube 57, which transfers the solid and liquid bone marrow to the collection device 56.

The apparatus 10 of FIGS. 1 and 2 could be used immediately before, during, or after a dental procedure or dental surgery. Thus, an adaption of the apparatus 10 described above which does not contain the rotating bur 38 is also in accordance with the present invention. Preferably, the rotating bur 38 incorporates an internal vacuum. More preferably, the configuration would be an entirely disposable unit designed to fit on a standard dental straight hand piece or to fit on a standard "E" motor, either air driven or electric.

A biopsy needle 85, shown schematically in FIG. 1, may be used in conjunction with the apparatus 10. One configuration for utilizing the biopsy needle 85 includes a tube 80 (FIG. 1) in communication with the valve 68 and the suction tube 57. The biopsy needle 85 may be connected at an end of the tube 80. The valve 68 may be used to control whether suction is produced through the tube 57 (and therefore the apparatus 10), the tube 80, or, if desired, both the tube 80 and the tube 57 simultaneously. When suction is produced in the tubes 57, 80 simultaneously, the biopsy needle 85 may be positioned adjacent the extraction site to provide extra suction and to otherwise assist the apparatus 10 in extracting bone marrow.

Alternatively, an end 90 of the tube 57 may be removed from the housing 17. A biopsy needle may be attached to the end 90 of the tube 57. The biopsy needle may then be positioned adjacent the extraction site to assist in bone marrow extraction. In this configuration, all suction would be provided by the biopsy needle, because the apparatus 10 would not be in communication with the vacuum source 74.

A preferred embodiment has a rotating bur 38 that is oversized for vacuum collection. The rotating bur 38 may be made of, for example, carbides, stainless steel, or plastic, and comprises at least one large opening similar to internal irrigating burs used for implants, with a cuff as either an integral part of a disposal hand piece or attachable to the bur 38, allowing free rotation of the forward portion only. The rotating bur 38 is connected to a vacuum hand piece similar to the housing 17, such as disclosed in U.S. Pat. No. 3,863,635. The rotating bur 38 may also be contained within the suction tube 57.

The liquid bone marrow can be obtained from dental extraction sites using a heavy metal blunt instrument following dental extraction to compress the bone alone and integrated vacuum to collect the bone marrow.

The apparatus 10 may include a solid bone marrow extraction portion having a first end and a second end. The first end is for collecting bone marrow. The apparatus 10 may also include a liquid bone marrow extraction portion comprising a first end and a second end. The first end is for breaking bone marrow stroma and aspirating the liquid marrow. Some conventional biopsy needles may be used to provide the solid bone marrow extraction portion and the liquid bone marrow extraction portion.

The apparatus of FIG. 2 may further comprise an elongated stainless steel solid marrow pushing probe to express a solid marrow specimen outside the cavity 26 after the procedure. One example is shown in U.S. Pat. No. 5,012,818.

The extraction of bone marrow from the jawbone during a dental procedure provides an advantage to the dental procedure alone in that it decreases the percentage of extraction sites experiencing dry sockets. This is due to the perforation of the compressed bone of the tooth socket.

In an exemplar embodiment, the bone marrow extraction apparatus effects the removal of bone marrow and bone marrow fluid from a donor and mixes the removed bone marrow with a suitable form of solution, such as a mixture of anticoagulant and saline or electrolytic solution. The bone marrow and bone marrow fluid removed from the donor are then transferred either into a cell separator or a suitable collection bag, such as the collection chamber 56, so as to permit separation of the bone marrow and fluid for subsequent processing and long-term storage. The collected bone marrow may also be used for the subsequent reinjection into the donor in future bone marrow transplantation procedures.

In the removal of the bone marrow from the donor, a solution consisting of heparin or other anticoagulant compositions, together with a saline solution, can be mixed with the bone marrow and bone marrow fluid before, during, and/or after being transferred into separating or collecting means.

The collection device 56 may be a bag containing chemicals for preserving bone marrow. The chemicals may be in the bag prior to the withdrawal of bone marrow from the jaw of a patient. In this manner, after bone marrow has been collected, the device 56 can be stored cold directly. Additionally or alternatively, chemicals can be added to the collection device 56 during or after collection of bone marrow to preserve the bone marrow. Suitable means for adding chemicals to a container such as the collection device 56 are well known in the art and may include penetrable membranes at specific locations on the collection device 56.

The collection device 56 is preferably collapsible so that air may be removed after collection has occurred. Removal of air increases the useful life of the bone marrow.

From the foregoing, disclosed is a bone marrow collection apparatus which is easily adapted to conventional dental or medical equipment. A technical advantage of the extraction-removing equipment of the invention is that bone marrow can be more quickly removed than conventional extraction procedures.

The dental apparatus according to the invention is not limited to that specifically disclosed and may comprise tools other than that described herein. Andre Schroeder et al., *Oral Implantology*, pages 66–71, 118–151, 178–187, 202–217, and 228–243 (George Thieme Verlag, 1988), discloses additional tools that are capable of boring holes in jawbones. Further, U.S. Pat. No. 4,564,374 discloses a device that is capable of extracting both solid and liquid bone marrow. Adaptation of this device may also be used in accordance with the present invention.

In an exemplar method, a donor is positioned in a dental examination chair. A hole is formed in the donor's jawbone before, during, or immediately after a conventional dental procedure using the boring portion or bur 38 of the apparatus according to the present invention. The boring portion or bur 38 can also be used to break up the bone marrow after a hole is formed. The area of marrow extraction is sterilized with an antiseptic solution. The entire procedure of obtaining both solid and liquid bone marrow can be accomplished in less than one to two minutes. The large lumen is introduced into the previously made bore hole and pushed into the medullary cavity. The large lumen is pushed further into the marrow cavity with forward pressure in order to obtain solid marrow. The large round bur can simultaneously irrigate and vacuum.

Liquid bone marrow sample is obtained by applying a negative pressure in the small lumen of the suction tube 57 using a vacuum source (not shown). This results in the breaking of marrow stroma and the release of fluid marrow.

Figure 5:
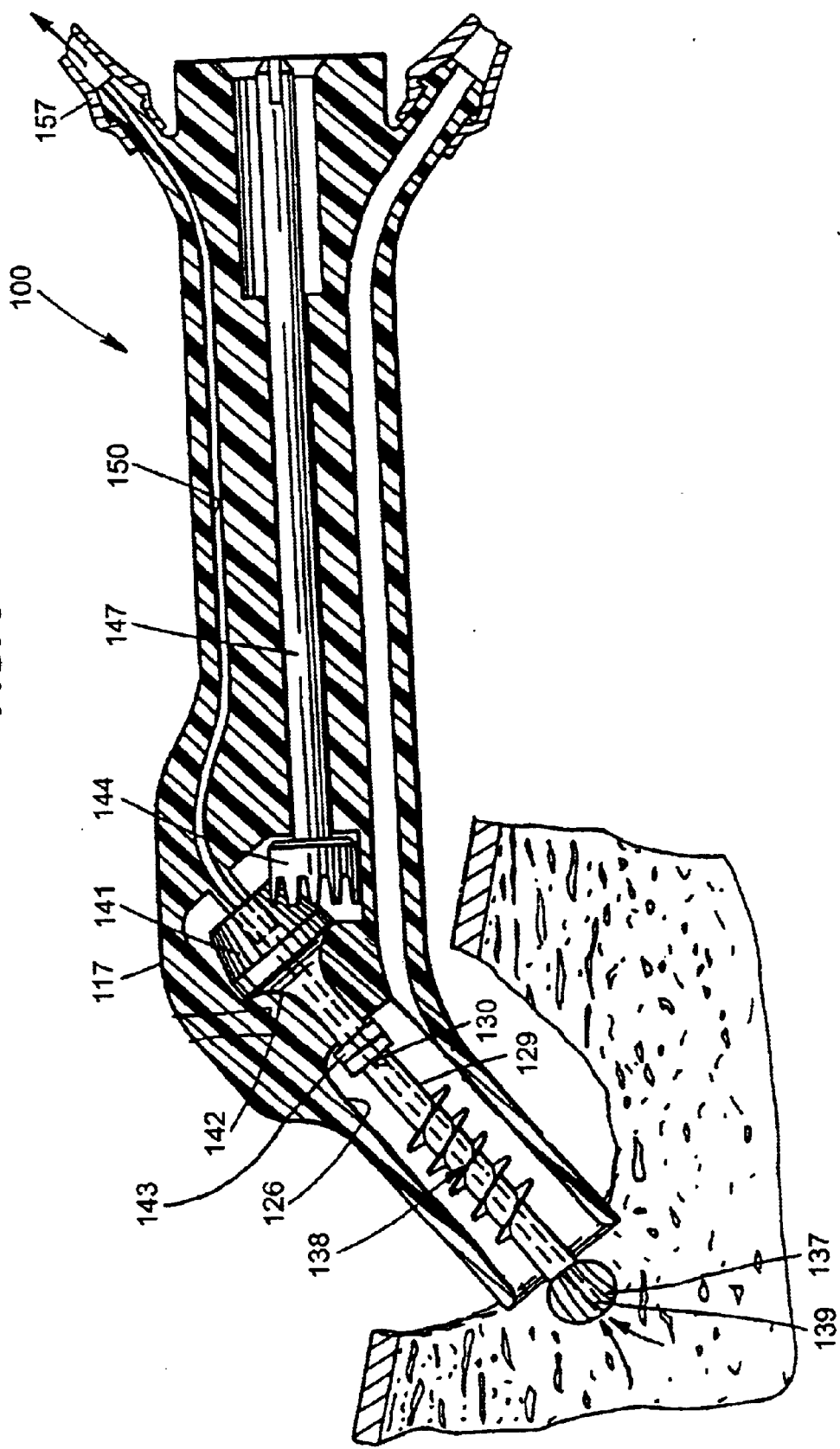
FIG. 5 is an enlarged, fragmentary sectional view of an alternative embodiment of the apparatus constructed in accordance with the teachings of the present invention.

Referring now to FIG. 5, an alternative embodiment of a bone material extraction device 100 is shown having a removable abrading means 138. As used herein, the phrase 'bone material' includes various hard bone materials (such as cortical bone), soft bone material (such as marrow), and contiguous tissue (such as dental pulp). The extraction device 100 includes a housing 117 through which a drive shaft 147 extends. As in the previous embodiments, an end of the drive shaft 147 is coupled to a motor (not shown) for rotating the shaft 147. A drive gear 144 is attached to an opposite end of the shaft 147 and is matingly engaged to a bevel gear 141. The bevel gear 141 includes an extension 142 having a connection end 143 disposed in a cavity 126 of the housing 117. While not shown in the illustrated embodiment, a reduction gear may be provided to obtain the desired rotational speed.

In the illustrated embodiment, the removable abrading means 138 is provided in the form of a bur having a bur head 137 attached to a shaft 129. The bur shaft 129 is removably attached to the connection end 143 of the extension 142 via threaded connection, a clamp, or any other releasable connection means known in the art. The bur head 137 is positioned on a distal end of the bur shaft 129 and includes a cutting flute 139 for boring into bone material. Accordingly, rotation of the drive shaft 147 is transferred via the drive gear 144, bevel gear 141, and extension 142 to the bur shaft 129, thereby to rotate the bur head 137.

The releasable connection provided by the removable bur 138 allows various types of burs to be used with the same hand piece housing 117. For example, a first bur having a large cutting flute may be used for cutting through and/or harvesting cortical bone. When a sufficient bone material extraction site has been created, the first bur may be replaced with a second bur having a larger lumen to more efficiently harvest softer bone material such as marrow. In addition, worn out burs may be more easily replaced.

In the embodiment of FIG. 5, a conduit 130 extends from the bur head 137 through the bur shaft 129 and extension 142 to a rear face of the bevel gear 141. A passage 150 extending through the housing 117 is placed in fluid communication with the conduit 130. A suction tube 157 may be connected to the passage 150 for extracting bone material from the extraction site. As a result, and in contrast to the previous embodiments, bone material is pulled through the conduit 130 formed in the bur shaft 129. The suction tube 157 is connected to a vacuum source and a collection device for storing the extracted bone material.

A second passage 153 may be formed in the housing 117 having one end in fluid communication with the cavity 126. A source of irrigation fluid may be connected to the housing 117 to provide irrigation fluid at the extraction site. The second passage 153 for irrigation is not required, and the device 100 may be used without irrigation in a variety of applications.

Figure 6:
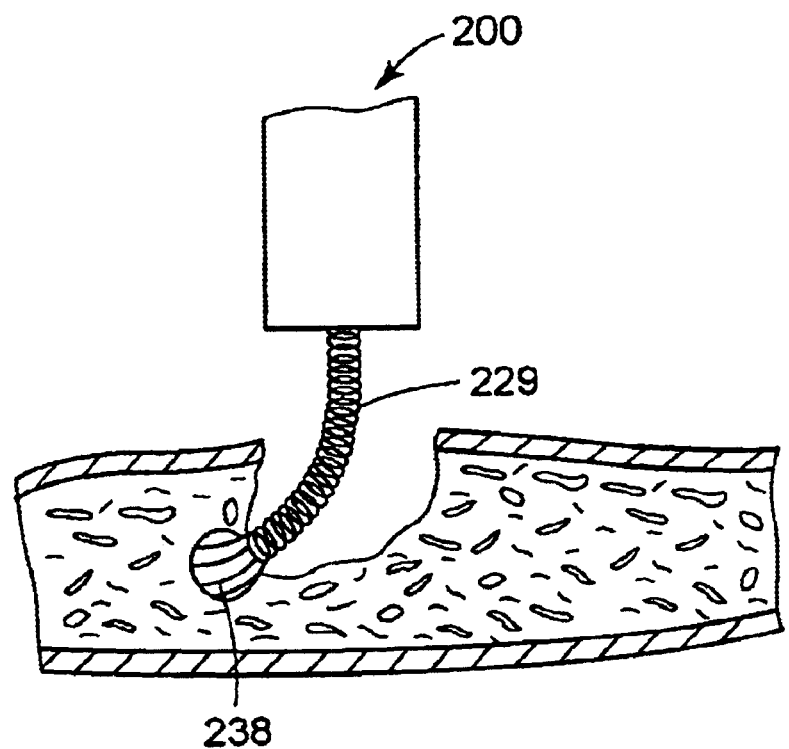
FIG. 6 is an enlarged, fragmentary side elevational view of yet another embodiment of an apparatus constructed in accordance with the present invention.

In a further embodiment illustrated in FIG. 6, an extraction apparatus 200 is shown that is suitable for use in relatively shallow bone material extraction sites. The apparatus 200 includes a bur 238 having a flexible shaft 229. As in the previous embodiment, a conduit extends through the shaft and fluidly communicates with a suction tube, so that loose bone material is pulled through the bur 238. The shaft 229 may be formed of plastic, solid metal, tightly wound spring, or other bendable material or structure. For certain structures, such as springs, the vacuum source must be sufficient to overcome the vacuum loss created by gaps in the shaft and still transport bone material through the bur 238. The flexible shaft 229 may be prestressed to bend in a desired direction. The bur 238 with flexible shaft 229 illustrated in FIG. 6 is particularly suited for collecting bone material from areas where the space between cortical layers is relatively narrow, such as from the skull and sternum. The flexible shaft 229 frees the bur head to move in a radial direction, thereby increasing the yield of bone material from a single entry point in the cortical bone layer.

Figure 8:
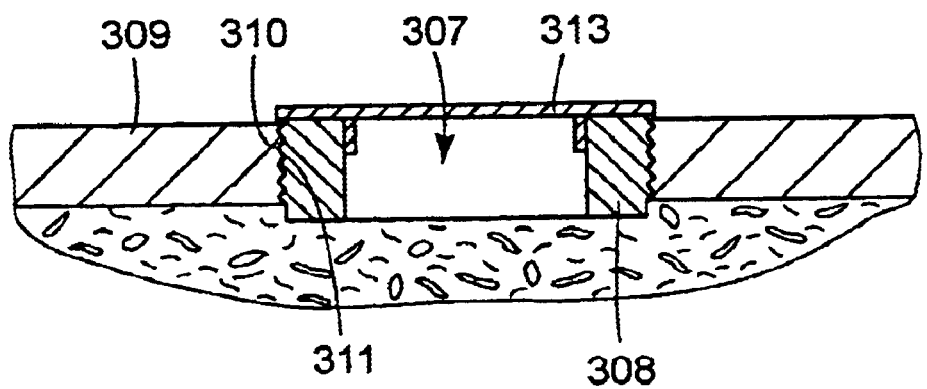
FIG. 8 is an enlarged side elevational view, in cross-section, of a collar and plug inserted into an entry port formed in a cortical bone layer.
Figure 7:
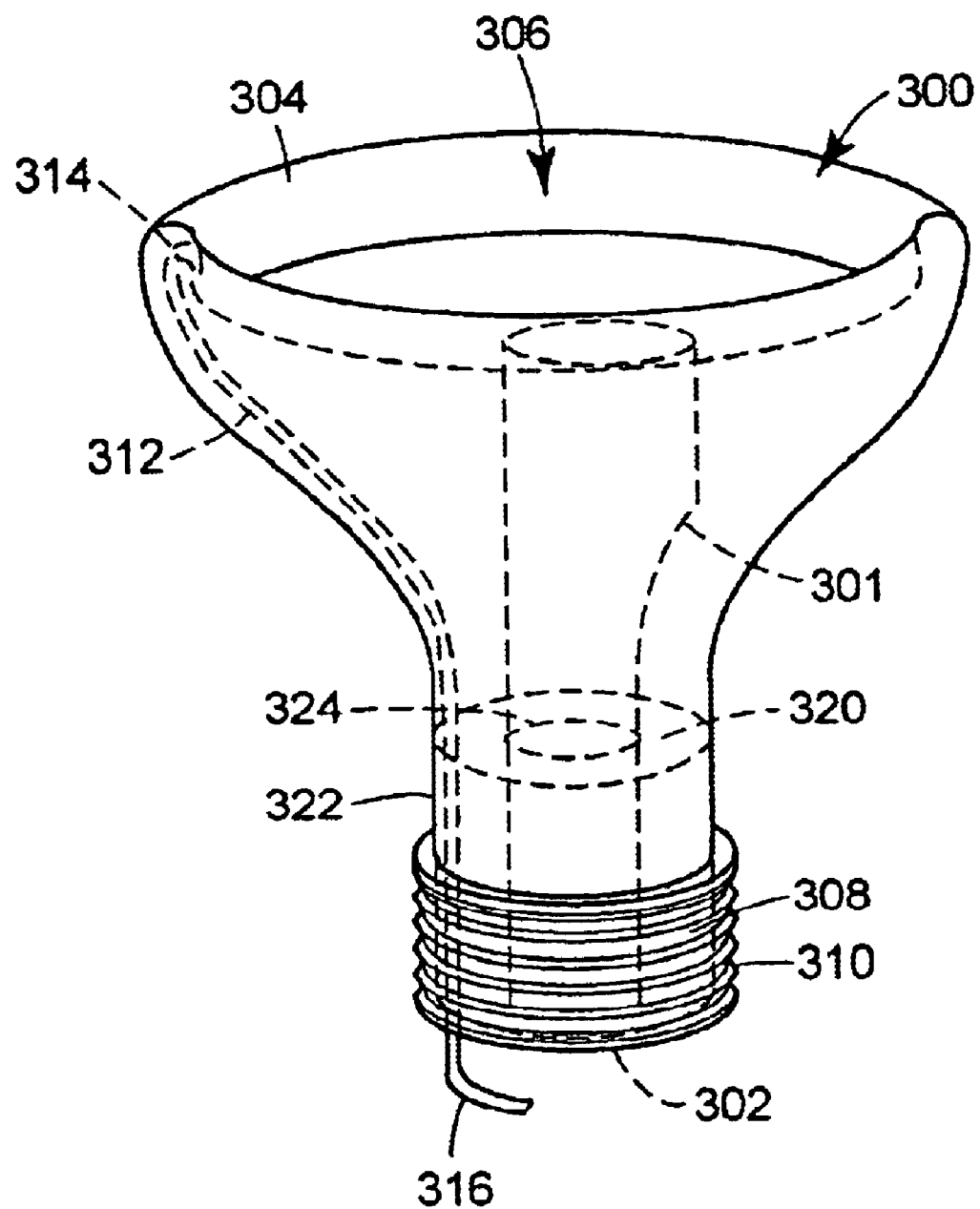
FIG. 7 is a perspective view of shield adapted for use with a bone marrow extraction apparatus.

FIG. 7 illustrates a shield 300 that may be used with an extraction apparatus 301 to assist in collecting bone material. The shield 300 may be formed of metal, plastic, or other materials. In an exemplar embodiment, the shield 300 is formed of a transparent, flexible material, such as silicone. The shield 300 has a connection end 302 and a receiving end 304. The receiving end 304 defines an opening 306 sized to receive at least a portion of an extraction apparatus hand piece. A collar 308, which may be in the form of an annular ring, is attached to the connection end 302 of the shield 300 and is sized for insertion into an entry port 307 formed in a cortical bone layer 309 (FIG. 8). The collar 308 includes releasable connection means, such as exterior threads 310 adapted to mate with complementary threads 311 in the entry port 307. Alternatively, the collar 308 may include retaining tabs, may be sized for an interference fit in the port 307, or may incorporate any other known releasable connection means.

The collar 308 may further be releasably attached to the shield 300 so that the collar 308 may remain in place in the entry port 307 after the extraction process is complete. Accordingly, the collar 308 may be formed of any material used to augment bone or to serve as a resorbable membrane, such as collagen. If the collar 308 is to remain indefinitely or permanently in place, a plug 313 (FIG. 8) formed of a similar material may be inserted into the collar 308 to close off the entry port 307.

The shield 300 may include a moveable arm 312 for directing the bur head of an extraction apparatus having a flexible bur shaft, as shown in FIG. 7. The moveable arm 312 includes a grip end 314 positioned near the shield receiving end 304 that may be grasped by the user and rotated about the inside surface of the shield 300. The arm 312 further has a directing tip 316 positioned proximal to the connection end 302 for engaging the bur shaft or head when the extraction apparatus is inserted into the shield 300. Accordingly, as the arm 312 is rotated about the shield 300, the directing tip 316 pushes the bur head toward a desired location and helps hold the bur head in the desired location as the bur shaft rotates.

A gasket 320 is provided in a neck portion 322 of the shield 300, as shown in FIG. 7. The gasket 320 defines an inner aperture 324 sized to closely fit a housing exterior of the extraction apparatus, thereby to assist in maintaining a sufficient vacuum level in the vicinity of the bur head.

In addition to the benefits noted above, the shield 300 stabilizes the positioning of the extraction apparatus during a collection procedure by providing support, via engagement of the housing by the gasket 320. The shield 300 may also help protect soft tissue when bone material is extracted from a site surrounded by such tissue.

From the foregoing, it will be appreciated that the extraction apparatus described herein may be used to harvest bone material from a variety of sites. As disclosed above, bone material may be extracted from the jaw, sternum, and skull. In addition, the apparatus may collect bone material from other sites, such as the hip. Furthermore, as noted above, contiguous tissue such as dental pulp is included in the definition of 'bone material', as used herein. The methods and apparatus disclosed herein may be used to extract dental pulp from exfoliated teeth, for example.

While a rotating bur has been described in the above embodiments, it will be appreciated that other bone material abrading means, such as a reciprocating file, may be used without departing from the scope of the present invention. Furthermore, while the illustrated burs are shown as being round, the abrading means, whether a bur, a file, or other device, may be in any shape or form suitable for abrading and extracting bone material.

The foregoing detailed description has been given for clearness of understanding only, and no unnecessary limitations should be understood therefrom, as modifications will be obvious to those skilled in the art.

What is claimed is:

1. Apparatus for extracting bone material from an extraction site, comprising:
    a housing defining a cavity and a passageway for transporting bone material to a collection device, the passageway having a distal end, in communication with a first end of a suction tube, and a proximal end; the housing further defining a second passageway for passing irrigation fluid to the extraction site, the apparatus further comprising a source of irrigation fluid in fluid communication with the second passage;
    a flexible shaft with a proximal end disposed in the cavity and a distal end extending beyond the cavity;
    an abrading head attached to the distal end of the shaft;
    a conduit extending through the shaft and abrading head, the conduit fluidly communicating with the passageway; and
    an actuator coupled to the proximal end of the shaft, wherein the shaft is free to deflect radially with respect to a connection to the actuator.

2. The apparatus of claim 1, in which the flexible shaft comprises a tightly wound spring.

3. The apparatus of claim 1, in which the flexible shaft is prestressed to bend in a predetermined direction.

4. The apparatus of claim 1, in which the abrading head comprises a bur and the actuator rotates the shaft.

5. The apparatus of claim 1, in which the abrading head comprises a bur and the actuator causes the shaft to move in a reciprocating motion.

6. The apparatus of claim 1, in which a drive member is disposed in the housing and is adapted for connection to the actuator, and the shaft second end is releasably connected to the drive member.

7. The apparatus of claim 1, in which a second end of the suction tube is connected to a vacuum source.

8. The apparatus of claim 1, in which the collection device comprises a container in fluid communication with the suction tube.

* * * * *